United States Patent [19]

Marchand et al.

[11] Patent Number: 4,997,629

[45] Date of Patent: Mar. 5, 1991

[54] ASSEMBLY FOR THE DISINFECTING OF TOOTHBRUSH

[76] Inventors: Paul Marchand, 1171 - 71st St., Miami Beach, Fla. 33141; Willard Marchand, 146 Stromboli, Venetian Shores, IslaMorada, Fla. 33036; Noel W. Abramson, 830 W. 32nd St., Hialeah, Fla. 33012; Stuart Rapee, 3620 Yacht Club Dr., TH 506, Miami, Fla. 33180

[21] Appl. No.: 500,895

[22] Filed: Mar. 29, 1990

[51] Int. Cl.[5] ............................................... A61L 2/20
[52] U.S. Cl. ................................. 422/300; 137/560; 422/305
[58] Field of Search .................. 422/1, 28, 29, 32; 422/300, 305; 137/560

[56] References Cited

U.S. PATENT DOCUMENTS

| | | | |
|---|---|---|---|
| 1,364,557 | 1/1921 | Hurley | 422/28 |
| 1,544,694 | 7/1925 | Speidel | 422/28 |
| 1,625,202 | 4/1927 | Gindick | 422/300 |
| 1,811,732 | 6/1931 | Pfeifer | 422/300 |
| 2,046,606 | 7/1936 | Borba | 422/300 |
| 2,099,336 | 11/1937 | Hart | 422/300 |
| 2,280,431 | 4/1942 | Hart | 422/300 |
| 3,342,544 | 9/1967 | Curiel | 422/300 |

FOREIGN PATENT DOCUMENTS 2451755 5/1976 Fed. Rep. of Germany ........ 422/28

*Primary Examiner*—Robert J. Warden
*Assistant Examiner*—Timothy M. McMahon
*Attorney, Agent, or Firm*—Malloy, Downey & Malloy

[57] ABSTRACT

An assembly for the disinfectant of one or more toothbrushes or like objects comprising a housing generally in the form of a canister for the containment of a supply of disinfectant composition preferably in fluid form wherein an applicator chamber is formed within the housing and the toothbrushes are also oriented therein such that the head and bristle portion thereof are disposed within the applicator chamber in fluid communication with disinfectant issuing from the supply. The disinfectant supply may be in the form of a pressurized aerosol container or any other applicable supply container and pump combination.

11 Claims, 2 Drawing Sheets

ASSEMBLY FOR THE DISINFECTING OF TOOTHBRUSH

BACKGROUND OF THE INVENTION

1. Field of the Invention

This invention relates to an assembly and/or container like housing for the selective disinfecting of toothbrush heads and bristles or similar objects by exposing the head portions to a fluid, liquid, aerosol or like disinfectant composition within the housing.

2. Description of the Prior Art

Structures exist in the prior art which are specifically designed for the disinfecting of at least the head portions of toothbrushes. Recent studies by the dental profession and/or toothbrush manufacturers have indicated that for proper oral hygiene and the overall health and well being of the toothbrush users, toothbrushes should be discarded after approximately a two week, if not properly disinfected, due to the buildup of bacteria.

From a health standpoint, it is commonly acknowledged that bacteria accumulates on the toothbrush and within the bristles of the brush head. Bacteria is collected directly from the user's mouth and also from exposure during storage between uses in a less than totally hygienic location such as on open racks within a bathroom or like facility.

If the toothbrush or more specifically, the head and bristle portion thereof were properly disinfected, discarding of the toothbrush, approximately every two weeks, would not be necessary. This is a significant factor for the development of an efficient and effective disinfectant structure or assembly since the replacement of a toothbrush approximately twenty-five times a year could be costly especially to the parent or head of a household of a large family.

Prior art attempts to overcome this problem have resulted in the use of ultra-violet light maintained within some type of canister or like chamber which was additionally structured to house one or more toothbrushes in an orientation which would expose the head and bristles of the toothbrushes directly to the ultra-violet light. Studies indicate that in order to effectively disinfectant the head of a toothbrush, the exposure to the ultra-violet light must be over an extremely long period of time. Such prolonged exposure is frequently not possible or may be inconvenient for the repeated use of any one of a plurality of toothbrushes within the disinfecting container. Also, the use of electrical equipment in bathrooms has been proven to be unpopular with most consumers due to the potential hazard of electrical shock. Of course, power consumption is an additional consideration.

In light of the above, there is therefore a recognized need in the industry for a device which will effectively and rapidly disinfect at least the head portion and attached bristles of a plurality of toothbrushes in a manner which will not involve the use of electrical energy. Such a device should be long lasting, free of any major repair or maintenance requirements and easy to operate even for relatively young children.

SUMMARY OF THE INVENTION

This invention relates to an assembly specifically designed to disinfect toothbrushes or at least the head portion and bristles attached thereto or more specifically, at least the portion of the toothbrush which enters the oral cavity during use. While the present invention is described hereinafter primarily with reference to the disinfecting of a toothbrush, it should be obvious that the intended scope of the present invention is meant to include other like objects.

More specifically, the subject assembly includes a housing having a hollow interior portion which at least partially defines an applicator chamber. In a preferred embodiment to be described in greater detail hereinafter, the housing includes a base in which a supply container of disinfectant material may be removably disposed. The base has an open end which communicates directly with a cap or cover portion of the housing wherein the cap and the base are removably attached to one another adjacent open end portions thereof. The aforementioned applicator chamber is primarily defined on the interior of the cap but, of course, could be located at other parts of the interior of the housing.

A support means in the form of a support tray or like structure is removably attached or mounted adjacent the open end of both the base and the cap portion and immediately adjacent the junction therebetween. The support tray is structured to include preferably a plurality of apertures transversely dimensioned to allow the passage of a conventional toothbrush therethrough such that the head and bristle portion thereof extends outwardly from what may be considered an upper portion of the support tray into the interior of the cap and applicator chamber. The handle portion of each of the supported toothbrushes extends through the support tray down into the interior of the hollow base and in somewhat surrounded relation to the supply container also maintained in the base.

A dispensing means is provided in connected, operative engagement with the supply container. The dispensing means may take the form of a valve structure which may include a conventionally structured aerosol type valve in the embodiment of the subject application where the supply container is in the form of a pressurized aerosol container. A valve stem of the valve assembly extends upwardly from an upper operative or dispensing end of the supply container substantially adjacent to the underportion of the support tray A dispensing nozzle is connected to the valve stem and is disposed in a proper orientation by passage through a central aperture in the support tray such that a plurality of dispensing apertures within the nozzle structure serves to somewhat equally dispense the composition from the interior of the supply container throughout the interior of the cap structure or applicator chamber. A somewhat loose fitting engagement between the nozzle structure and the interior surfaces of the central aperture of the support tray will serve to effectively maintain the supply container within the hollow base portion of the housing and eliminate inadvertent displacement.

Another feature of the present invention includes an activating means preferably mounted in the cap structure and disposed in cooperative, activating relation to the nozzle and valve assembly attached thereto. More specifically, the activating means includes a push button or like manually activatable structure movably mounted on the cap and being exteriorly accessible so that the user of the device can readily push or otherwise manipulate the push button into activating contact with the nozzle and attached valve structure. Forced engagement of the push button or more specifically, an interior portion thereof will serve to depress or otherwise position the nozzle and accompanying valve structure in an operative, dispensing position for release of the disinfectant composition within the supply container through the nozzle and throughout the interior of the closed, substantially sealed applicator chamber into contact with the heads of the toothbrushes as well as the bristles associated therewith.

In addition to the above, vent means in the form of one or more apertures may be placed at any applicable location in the walls of the base or cap portion of the housing in order to properly vent the housing to atmosphere. When such vent means is utilized, there may also be provided a filter structure which is specifically designed to substantially cover any vent apertures in the housing and thereby eliminate the entry of any bacteria therethrough.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
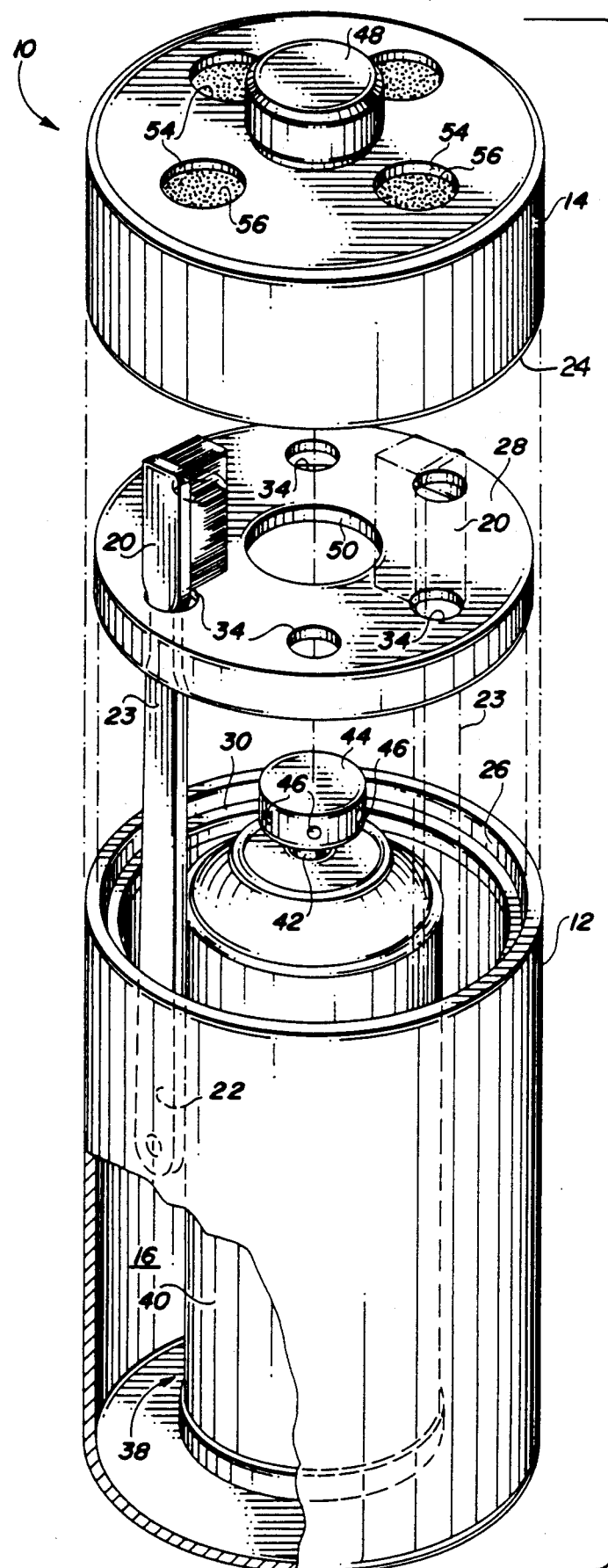
FIG. 1 is a perspective view in partial cutaway and exploded form showing the various components of the assembly of the present invention.
Figure 3:
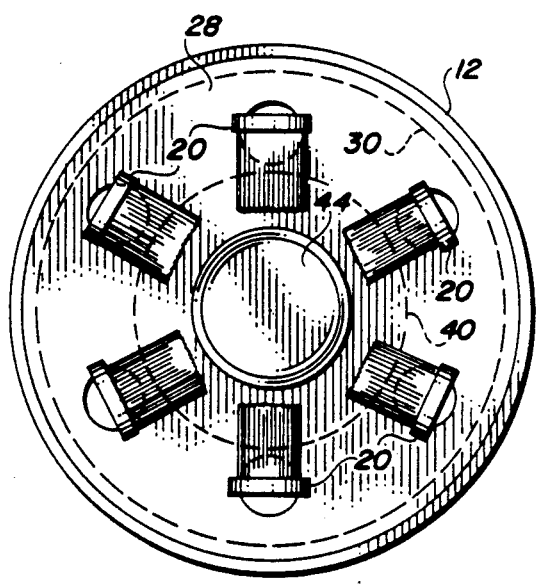
FIG. 3 is a sectional view taken along line 3—3 of FIG. 2.
Figure 2:
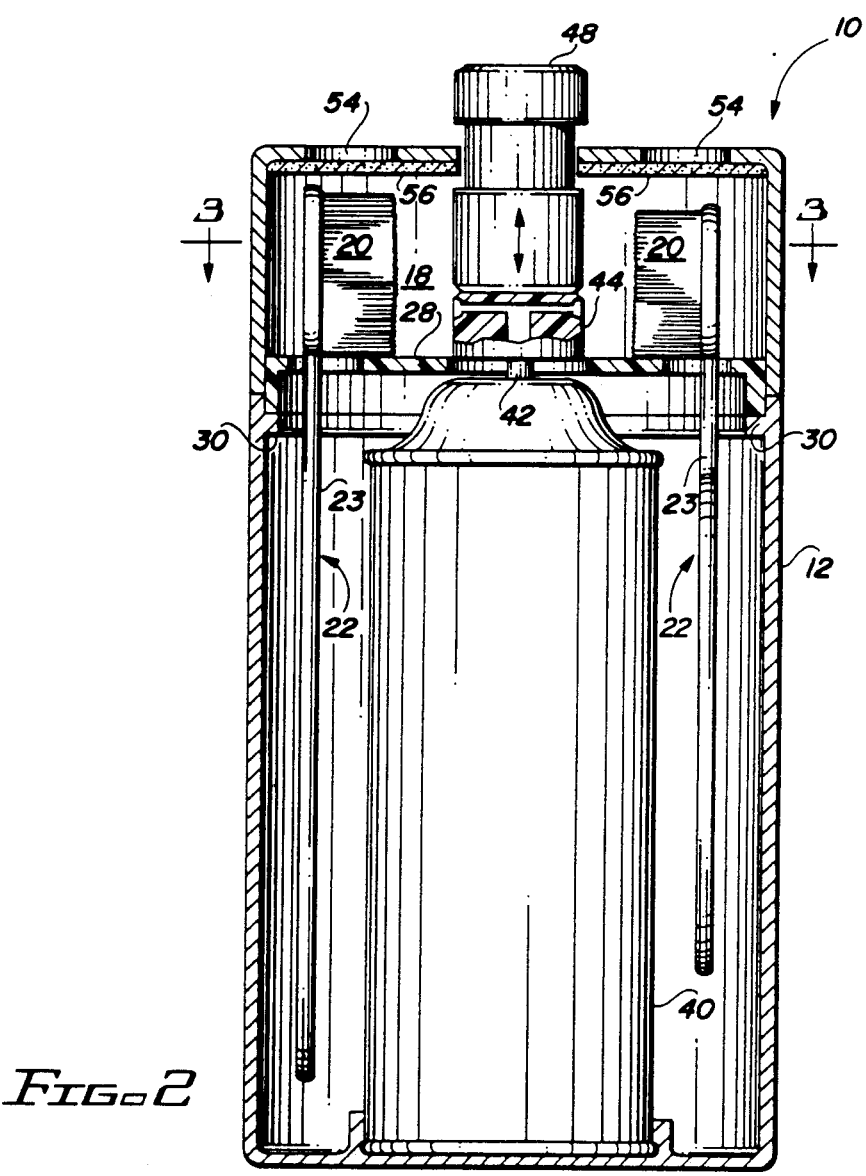
FIG. 2 is a longitudinal sectional view in partial cutaway showing the components of the subject assembly in assembled position.

As shown in FIGS. 1 through 3, the present invention is directed towards an assembly generally indicated as 10 including a housing defined by a base portion 12 and a cap or cover portion 14, both the base 12 and the cap 14 include a substantially hollow interior portion as at 16 and 18 respectively. The hollow interior portion 18 of the cap may define an applicator chamber in which the head and bristle portion 20 of a toothbrush 22 is disposed during the disinfecting procedure. Both the base 12 and the cap 14 terminate in correspondingly positioned open ends as at 24 and 26 respectively. These open ends have peripheral configurations which cooperate to allow removable support of the cap 14 on the base 12 as clearly shown in FIG. 2. Attachment therebetween may be in the form of any somewhat standard attachment such as a threaded connection and/or a slideable friction type engagement.

A toothbrush support means in the form of a support tray 28 is removably mounted generally on the interior of the base 16 immediately adjacent the open end 26. Such attachment may be by means of an integrally or otherwise fixedly mounted support ring or like member 30 secured to the inner surface of the base 12 and disposed to supportingly engage the undersurface of the support tray 28. The support tray 28 includes a plurality of mounting openings or apertures 34 extending through the support tray 28 and being transversely dimensioned to allow the passage of the handle portion 23 of the supported toothbrushes 22 to pass therethrough. However, the dimension and overall configuration of the apertures 34 prevent the passage of the enlarged head and bristle portion 20 of the toothbrush as clearly shown in both FIGS. 1 and 2. This serves to support each of the toothbrushes in a somewhat upright position. More importantly, the supported orientation of the toothbrushes 22 will serve to position the head and bristle portion 20 within the applicator chamber defined on the interior 18 of the cap 14.

As set forth above, the support tray 28 is removable from its operative position as clearly shown in FIG. 1 in order to provide placement and removal of a supply of disinfectant generally indicated as 38. The supply of disinfectant may be in the form of a container as at 40 which, in a preferred embodiment, is further defined by a pressurized aerosol container.

Replacement of the container 40 is therefore accomplished on a periodic basis after the supply of disinfectant has been used by merely removing the cap 14 and support tray 28 and replacing the container 40 with a fresh supply.

The invention further includes dispensing means in the form of a valve structure associated directly with the container 40 and which is represented by valve stem 42 communicating with the interior of the container 40. As set forth above, in the preferred embodiment, the container 40 is a pressurized aerosol container. Therefore, depression or other predetermined manipulation or displacement of the valve stem 42 will cause the contained disinfectant to pass from the interior of the container 40 through the valve stem and out through a nozzle structure 44. The nozzle structure 44 may also be considered part of the dispensing means and in another embodiment, may include a plurality of evenly spaced dispensing apertures 46. The array of dispensing apertures 46 serves to substantially evenly distribute the dispensed disinfectant from the valve stem 42 substantially evenly throughout the applicator chamber or interior 18 of the cap 14. All of the head and bristle portions 20 of the toothbrushes will therefore be exposed to the disinfectant material once the nozzle 44 and connected valve stem 42 is operatively displaced for dispensing.

Dispensing and/or operative manipulation of the nozzle 44 and valve stem 42 occurs by pressing or otherwise manipulating a push button or like actuator member 48 which may define a portion of an activating means associated with the present invention. More specifically, the push button 48 is exteriorly accessible on the cap 14 and is spring biased as best shown in FIG. 2. This spring bias mounting will normally serve to position the push button 48 in an outwardly extended "ready" position. However, depression of the button will serve to move the button 48 against the nozzle serving to depress or otherwise position the nozzle and the attached valve stem 44 and 42 respectively into the dispensing or activating position. Disinfectant will there flow from the interior of the container 40 through the valve stem 42 and out the plurality of apertures 46 for even dispersion of the disinfectant throughout the applicator chamber and onto any of a plurality of head and bristle portions 20 mounted within the applicator chamber on support tray 28.

In order to properly position and somewhat restrain the supply container 40, an aperture 50 is provided within the support tray 28 in aligned registry with the nozzle 44. Both the nozzle 44 and the aperture 50 have a somewhat congruent configuration such that the nozzle is allowed to effectively pass, at least in part, through the aperture 50 and somewhat be retained thereby as best shown in FIG. 2. Inadvertent displacement of the container 40 will therefore be prevented through this engagement.

Yet another feature of the present invention is the provision of vent means in the form of one or more apertures 54 formed in an applicable portion of the wall of either the base 12 or cap 14 of the housing. These apertures 54 are provided to allow venting of the interior of the applicator chamber to atmosphere. However, in order to prevent the entry of any air born bacteria, some type of filter material as at 56 may be removably attached in overlying or covering relation to the venting apertures 54. Typically, the filter material 56 can be of the type from which paper like material face masks are formed wherein such face masks are typically used by dentists while treating a patient.

Further, the disinfectant composition maintained within the interior of the container 40 may, of course, be a variety of commercially available disinfectant compositions preferably including an alcohol base to accomplish rapid evaporation. One example of such composition would sodium benzoate in a liquid or other fluid type form adequate for manual pumping or for use in combination with a pressurized aerosol container 40 and valve structure 42.

Now that the invention has been described,
What is claimed is:

1. An assembly designed to disinfect toothbrushes, said assembly comprising:
   a. a housing including a hollow base portion having an open end and a hollow interior cavity,
   b. support means connected to said base portion and disposed and structured for support of a head portion of one or more toothbrushes within said housing,
   c. said housing further including a cap portion removably secured to said open end of said base portion substantially adjacent to said support means and in substantially sealed, surrounding and covering relation to the toothbrush heads so as to define an applicator chamber therein,
   d. a supply of disinfectant material removably mounted within said hollow interior cavity of said base portion below said support means and in segregated relation to said applicator chamber and the toothbrush head portions therein,
   e. dispensing means including a valve structure connected to said supply and being disposed and structured to deliver disinfectant from said supply in multiple directions simultaneously to within said applicator chamber and the toothbrush heads therein,
   f. activating means mounted on said cap portion in an exteriorly accessible location and disposable into activating engagement with said dispensing means, and
   g. whereby disinfectant is selectively disposed from said supply into said applicator chamber and onto each of the toothbrush heads therein upon disposition of said activating means into engagement with said dispensing means.

2. An assembly as in claim 1 wherein said housing comprises vent means formed in an outer wall thereof and structured for establishing fluid communication between the exterior and interior of said housing.

3. An assembly as in claim 2 further comprising filter means mounted adjacent said vent means and disposed and structured for filtering air passing through said vent means.

4. An assembly as in claim 1 wherein said support means comprises a support tray mounted adjacent to a junction of said cap portion and a remainder of said housing and structured to hold a plurality of toothbrushes in an orientation which positions the head portions of the toothbrush within said chamber in covered relation by said cap.

5. An assembly as in claim 4 wherein said activating means comprises a depressible push button mounted on said cap and exteriorly accessible thereon, said push button including an inner portion positionable in activating engagement with said valve structure within said chamber upon depression thereof.

6. An assembly as in claim 5 wherein said supply comprises an aerosol container having disinfectant composition contained therein.

7. An assembly as in claim 1 wherein said support means comprises a support tray structured to hold a plurality of toothbrushes in an upright orientation, said support tray disposed in covering relation to said open end of said base between said base and said cap structure, said base dimensioned to receive handle portions of the toothbrushes within said hollow interior cavity of said base and head portions thereof within said chamber.

8. An assembly as in claim 7 wherein said dispensing means further comprises a nozzle mounted on said valve structure within said chamber, said nozzle structured to distribute disinfectant from said supply to within said chamber and brush heads positioned therein.

9. An assembly as in claim 8 wherein said support tray comprises a central opening dimensioned and disposed to allow passage therethrough of said nozzle into aligned, engageable relation with said activating means.

10. An assembly as in claim 9 wherein said activating means comprises a depressible push button mounted on said cap and exteriorly accessible thereon, said push button including an inner portion positionable in activating engagement with said nozzle within said chamber upon depression thereof.

11. An assembly as in claim 10 wherein said supply comprises an aerosol container including disinfectant composition contained therein.

* * * * *